US009036771B2

(12) United States Patent
Yu et al.

(10) Patent No.: US 9,036,771 B2
(45) Date of Patent: May 19, 2015

(54) SYSTEM AND METHOD FOR DENOISING MEDICAL IMAGES ADAPTIVE TO LOCAL NOISE

(71) Applicants: Lifeng Yu, Byron, MN (US); Armando Manduca, Rochester, MN (US); Zhoubo Li, Rochester, MN (US); Joel G. Fletcher, Oronoco, MN (US); Cynthia H. McCollough, Byron, MN (US)

(72) Inventors: Lifeng Yu, Byron, MN (US); Armando Manduca, Rochester, MN (US); Zhoubo Li, Rochester, MN (US); Joel G. Fletcher, Oronoco, MN (US); Cynthia H. McCollough, Byron, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 208 days.

(21) Appl. No.: 13/762,141

(22) Filed: Feb. 7, 2013

(65) Prior Publication Data
US 2013/0202080 A1   Aug. 8, 2013

Related U.S. Application Data

(60) Provisional application No. 61/595,999, filed on Feb. 7, 2012.

(51) Int. Cl.
*A61B 6/00* (2006.01)
*G06T 11/00* (2006.01)
*A61B 6/03* (2006.01)

(52) U.S. Cl.
CPC .............. *G06T 11/003* (2013.01); *A61B 6/032* (2013.01); *A61B 6/5258* (2013.01); *A61B 6/5205* (2013.01); *A61B 6/542* (2013.01); *A61B 6/583* (2013.01)

(58) Field of Classification Search
CPC ................ G06T 2207/10081; G06T 11/005; A61B 6/5205; A61B 6/5211
USPC ....................... 378/19, 62, 108; 382/128–131
See application file for complete search history.

(56) References Cited

U.S. PATENT DOCUMENTS

| | | |
|---|---|---|
| 6,829,323 B2 | 12/2004 | Toth et al. |
| 7,657,074 B2 | 2/2010 | Haras |
| 2011/0286651 A1* | 11/2011 | Yu et al. .................... 382/131 |

OTHER PUBLICATIONS

Boedeker, et al., Application of the Noise Power Spectrum in Modern Diagnostic MDCT: Part I. Measurement of Noise Power Spectra and Noise Equivalent Quanta, Physics in Medicine and Biology, 2007, 52:4027-4046.

Ciaschini, et al., Urinary Calculi: Radiation Dose Reduction of 50% and 75% at CT—Effect on Sensitivity, Radiology, 2009, 251:105-111.

Gies, et al., Dose Reduction in CT by Anatomically Adapted Tube Current Modulation. I. Simulation Studies, Medical Physics, 1999, 26:2235-2247.

Gooben, et al., Medical X-Ray Image Enhancement by Intra-Image and Inter-Image Similarity, Medical Imaging 2009: Image Processing, Proc. of SPIE, vol. 7259, pp. 72590G-1-72590G-10.

(Continued)

*Primary Examiner* — Courtney Thomas
(74) *Attorney, Agent, or Firm* — Yakov Sidorin; Quarles & Brady LLP

(57) ABSTRACT

A system and method is provided for estimating the local noise of CT images and denoising the images using a modified non-local means (NLM) algorithm that is adaptive to local variations of noise levels. A strategy for efficiently estimating the local noise of CT images is also described.

11 Claims, 2 Drawing Sheets

(56) References Cited

OTHER PUBLICATIONS

Li, et al., Simulating Low Dose CT Scans by Noise Addition, In Nuclear Science Symposium Conference Record, 2002 IEEE, vol. 3, pp. 1832-1834.

Manduca, et al., Projection Space Denoising with Bilateral Filtering and CT Noise Modeling for Dose Reduction in CT, Medical Physics, 2009, 36:4911-4919.

Massoumzadeh, et al., Validation of CT Dose-Reduction Simulation, Medical Physics, 2009, 36(1):174-189.

Pan, et al., Image Reconstruction with Shift-Variant Filtration and Its Implication for Noise and Resolution Properties in Fan-Beam Computed Tomography, Medical Physics, 2003, 30(4):590-600.

Wang, et al., Penalized Weighted Least-Squares Approach to Sinogram Noise Reduction and Image Reconstruction for Low-Dose X-Ray Computed Tomography, IEEE Trans. Med. Imaging, 2006, 25(10):1272-1283.

Wang, et al., Virtual Colonoscopy Screening with Ultra Low-Dose CT: A Simulation Study, IEEE Nuclear Science Symposium Conference Record, 2007, pp. 4564-4568.

Whiting, et al., Properties of Preprocessed Sinogram Data in X-Ray Computed Tomography, Medical Physics, 2006, 33(9):3290-3303.

Wunderlich, et al., Image Covariance and Lesion Detectability in Direct Fan-Beam X-Ray Computed Tomography, Phys. Med. Biol., 2008, 53(10):2471-2493.

\* cited by examiner

SYSTEM AND METHOD FOR DENOISING MEDICAL IMAGES ADAPTIVE TO LOCAL NOISE

CROSS-REFERENCE TO RELATED APPLICATIONS

The present application is based on, claims priority to, and incorporates herein by reference in its entirety U.S. Provisional Patent Application No. 61/595,999, filed Feb. 7, 2012, and entitled "SYSTEM AND METHOD FOR CONTROLLING RADIATION DOSE FOR RADIOLOGICAL APPLICATIONS."

BACKGROUND OF THE INVENTION

The present invention relates to medical imaging and, more particularly, to systems and methods for controlling radiation doses delivered when performing imaging processes using ionizing radiation.

In a computed tomography system, an x-ray source projects a beam which is collimated to lie within an X-Y plane of a Cartesian coordinate system, termed the "imaging plane." The x-ray beam passes through the object being imaged, such as a medical patient or other non-medical patient or object, such as in industrial CT imaging, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile at a particular view angle.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view", and a "scan" of the object comprises a set of views acquired at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique, however, other image reconstruction processes are also well known. This process converts the attenuation measurements from a scan into integers called "CT numbers" or "Hounsfield units", which are used to control the brightness of a corresponding pixel on a display.

The drastically increased use of CT in modern clinical settings has generated serious public health concerns regarding the cancer risks associated with the radiation exposure from CT.

The current guiding principle in CT clinical practice is to use radiation dose levels as low as reasonably achievable while maintaining acceptable diagnostic accuracy. However, lowering radiation dose alone generally produces a noisier image and may seriously degrade diagnostic performance. Many algorithms have been proposed for controlling noise in CT, and these can be broadly categorized into 3 major types: projection space, image space, and iterative reconstruction.

Projection space techniques, which work on either the raw projection data or the log-transformed sinogram, attempt to reduce noise in the projection data domain prior to image reconstruction. In general, these techniques have the advantage that noise properties in projection space are fairly well understood. One potential drawback of projection-based methods is that they may result in some loss of image sharpness due to the fact that edges in projection data are not well-defined.

Image-space denoising involves applying linear or non-linear filters directly to the reconstructed images. Most such techniques (e.g. bilateral filtering, total variation denoising, non-local means denoising, and k-SVD denoising) take advantage of the strong structural and statistical properties of objects in image space (e.g. sharp edges, similarities between neighboring pixels). In CT, they can be implemented directly and without access to the raw data. However, CT noise in image space is difficult to model accurately and has strong spatial variations and correlations. It can therefore be more difficult for such techniques to achieve an optimal tradeoff between denoising and blurring or artifacts, or to get consistent performance across an entire scan volume.

Iterative reconstruction (IR) techniques are more accurately considered reconstruction rather than denoising techniques, and take advantage of statistical assumptions about the noise properties in projection space and structure in image space. IR techniques require access to the raw data and accurate knowledge of the details of the scanner geometry, photon statistics, data-acquisition and correction physics, thus highly dependent on specific scanner models. True IR is very computationally intensive (e.g., several hours per data set), which has prevented fast clinical application to date, although software methods and hardware methods have been investigated to accelerate the iterative procedure.

Due to the extremely high computational load of true IR, hybrid techniques have recently been developed that attempt to gain many of the benefits of true IR with much lower computational load (e.g. Sinogram AFirmed Iterative REconstruction (SAFIRE) from Siemens). Some of these are now available commercially, but whether they can achieve similar level of image quality improvement as true IR desire more physics and clinical evidence.

Despite the development of various IR methods, each is only available on some of the latest scanner models from each manufacturer. A large percentage of scanners currently in use in hospitals all over the world do not have these options. Our invention addresses the need for a denoising strategy that can be broadly used across the CT community, over a heterogeneous scanner fleet that encompasses different manufacturers as well as different models of varying age and software revision. These requirements lead us to consider image space denoising techniques, which are relatively simple to implement, work on the image data alone, and can be applied retrospectively. As mentioned above, it is difficult for image space techniques to model CT noise or scanner details accurately, and thus they may appear to necessarily be at a disadvantage with respect to projection space or IR methods. However, the spatial structure models in modern image denoising algorithms are significantly more advanced than the spatial regularization terms that are incorporated in current IR methods. It is thus not at all clear that image space results will necessarily be inferior.

Non-local means (NLM) denoising is an effective image denoising strategy that exploits the inherent redundant information present in most images. NLM generalizes the notion of finite spatial differences and utilizes a measure of difference between nearby image patches to estimate underlying image structure. This allows NLM to preserve a high degree of image texture and fine detail. However, the standard NLM algorithm uses a uniform filtering strength to denoise the image, while in CT images the noise level varies significantly within and across slices. Therefore, applying NLM filtering to CT images using a global filtering strength cannot achieve optimal denoising performance.

SUMMARY OF THE INVENTION

The present invention overcomes the aforementioned drawbacks by providing a system and method that can efficiently estimate the local noise of CT images, and denoise the images using a modified non-local means (NLM) algorithm that is adaptive to local variations in noise (for example, variations in noise levels).

In accordance with yet another aspect of the invention, a method for reconstructing an image acquired by delivering an irradiating dose of radiation to a subject is disclosed that includes obtaining a set of medical imaging data using the irradiating dose of radiation, obtaining a map of local noise (for example, noise level) in the medical imaging data, utilizing at least one of a non-local means filter adapted using the map of local noise to produce denoised medical imaging data, a bilateral filter, and an anisotropic diffusion filter.

In accordance with still another aspect of the invention, a computed tomography (CT) imaging system is disclosed that includes an x-ray source configured to emit x-rays toward an object to be imaged, a detector configured to receive x-rays that are attenuated by the object, a data acquisition system (DAS) connected to the detector to receive an indication of received x-rays, and a computer system coupled to the DAS to receive the indication of the received x-rays. The computer system is programmed to obtain a set of medical imaging data using the irradiating dose of radiation (which is delivered, for example, by the x-ray source), obtain a map of local noise in the medical imaging data, and utilize a non-local means filter adapted using the map of local noise to produce denoised medical imaging data. In a related implementation, the computer system is additionally or alternatively programmed to select at least one of a plurality of mechanisms for reducing image noise and reducing the dose of irradiating radiation that could be delivered to the subject to acquire an additional set of medical imaging data. Optionally, the computer system is also programmed to govern at least one of (i) insertion of noise into the medical imaging data to simulate the at least one of the plurality of mechanisms for reducing the dose of irradiating radiation that could be applied to acquire the additional set of medical imaging data to thereby generate a simulated set of medical imaging data at a reduced does of irradiating radiation; and (iii) reconstruction of a simulated reduced dose image from the simulated set of medical imaging.

Various other features of the present invention will be made apparent from the following detailed description and the drawings.

DETAILED DESCRIPTION OF THE INVENTION

Figure 1A:
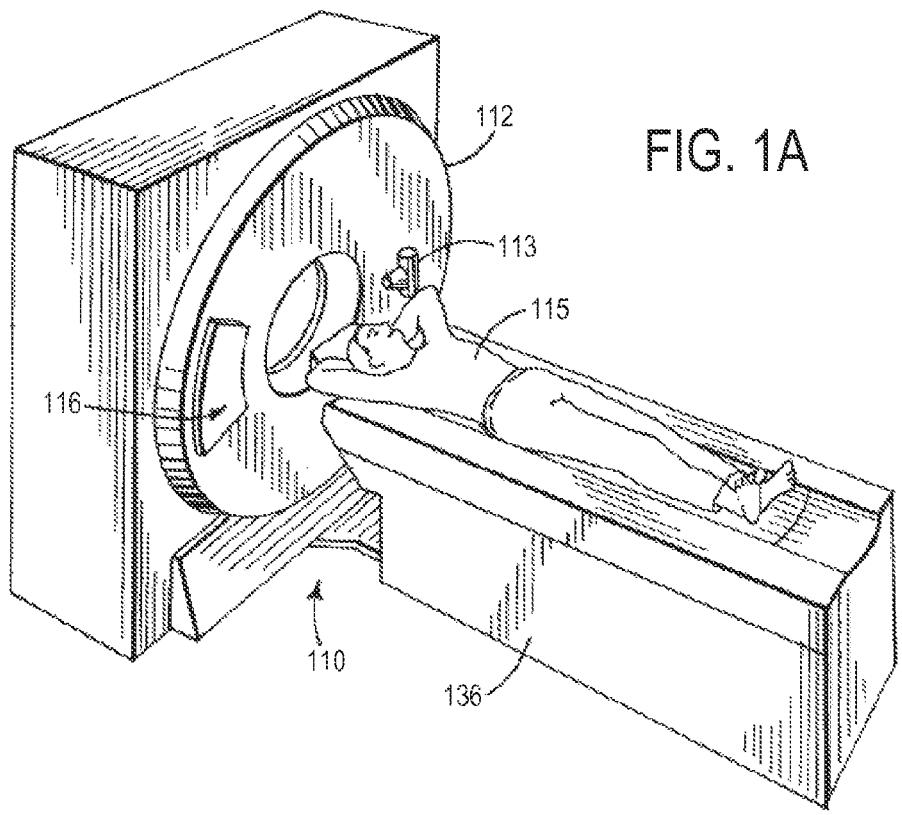
FIG. 1A is a CT imaging system in which the present invention may be employed.
Figure 1B:
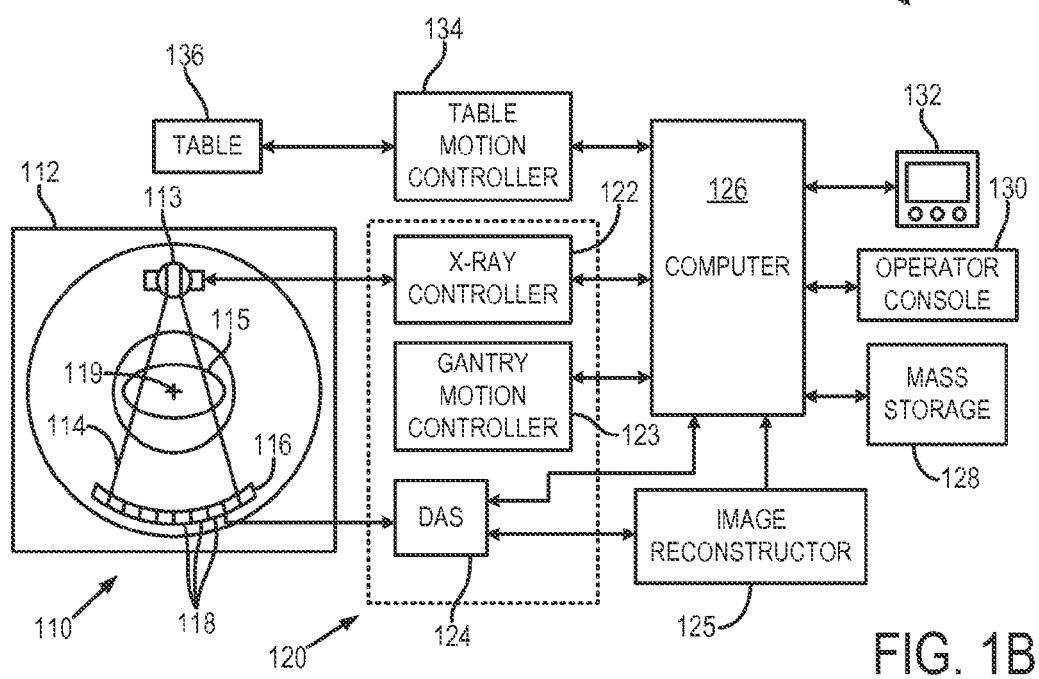
FIG. 1B is block schematic diagram of the CT imaging system of FIG. 1A.

With initial reference to FIGS. 1A and 1B, a computed tomography (CT) imaging system 110 includes a gantry 112 representative of at least a "third generation" CT scanner. In the illustrated example, the gantry 112 has a pair of x-ray sources 113 that each project a fan beam or cone beam of x-rays 114 toward a detector array 116 on the opposite side of the gantry 112. The detector array 116 is formed by a number of detector elements 118 that together sense the projected x-rays that pass through a medical patient 115. During a scan to acquire x-ray projection data, the gantry 112 and the components mounted thereon rotate about a center of rotation 119 located within the patient 115 to acquire attenuation data.

The rotation of the gantry 112 and the operation of the x-ray source 113 are governed by a control mechanism 120 of the CT system 110. The control mechanism 120 includes an x-ray controller 122 that provides power and timing signals to the x-ray sources 113 and a gantry motor controller 123 that controls the rotational speed and position of the gantry 112. A data acquisition system (DAS) 124 in the control mechanism 120 samples analog data from detector elements 118 and converts the data to digital signals for subsequent processing. An image reconstructor 125, receives sampled and digitized x-ray data from the DAS 124 and performs high speed image reconstruction. The reconstructed image is applied as an input to a computer 126 that stores the image in a mass storage device 128.

The computer 126 also receives commands and scanning parameters from an operator via console 130 that has a keyboard. An associated display 132 allows the operator to observe the reconstructed image and other data from the computer 126. The operator supplied commands and parameters are used by the computer 126 to provide control signals and information to the DAS 124, the x-ray controller 122, and the gantry motor controller 123. In addition, computer 126 operates a table motor controller 134 that controls a motorized table 136 to position the patient 115 in the gantry 112.

A non-local means (NLM) filter in accordance with the present disclosure assumes that images contain a substantial amount of redundant local structure, and this property can be exploited to reduce noise by performing weighted averages of pixel intensities. The weights are based on calculations of the form:

$$w(i, j) = \exp\left(-\frac{\sum_{\delta \in P} G_\sigma(\delta)[v(i+\delta) - v(j+\delta)]^2}{h^4}\right),$$

where G is a Gaussian kernel of variance $\sigma^2$, P denotes the patch centered at positions i, j, and the weight between two pixels is calculated by computing the summed squared intensity difference of all pixels in the two patches. h is a smoothing parameter used to control the amount of denoising and is usually taken to be proportional to the assumed or known noise level. The standard NLM filter assumes that noise in image is spatially invariant and thus h is a global constant. For convenience below, we normalize the sum squared difference calculation by dividing by the number of pixels in a patch to express average sum squared difference per pixel, making h independent of the patch size. We also generally find it more effective to apply the filter in 3D, in which case image patches are generalized to image blocks and pixels are termed voxels.

In CT the noise level varies within and across slices, often by 2× within a slice and as much as 3× across slices. This implies that NLM denoising based on a single noise level may be too weak in some places (accomplishing little), too strong in others (blurring fine detail), or both. It is therefore desirable to modify the NLM algorithm to adapt to the local noise level. Here we have adjusted the strength of h=k*SD locally, where SD is the estimated noise level of the pixel being denoised and k is the proportionality factor. This can be integrated in the filtering technique described above and involves little additional computational effort. We maintain a single k throughout the whole volume so that h varies proportionally to the local SD. Other variations about how to adapt to local noise level can also be used. It can be seen that this adaptive NLM filter uses a map of the local noise level, which in turn relies upon developing a way to efficiently estimate such a map, from image data alone, in a time compatible with the clinical workflow.

The CT image noise distribution can be estimated or calculated using many different approaches. Repeating scans multiple times for the same object is advantageous but extremely difficult to implement on patients. Another approach is through Monte Carlo simulation, adding simulated noise to raw data and reconstructing multiple realizations of CT images. However, this method relies upon access to the raw data, and a large number of repeated noise simulations and reconstructions, which is time consuming and makes it difficult to meet the clinical workflow requirement. An alternative approach is to derive the noise distribution analytically by propagating a noise model through the reconstruction equations. This has been implemented in simple fan-beam CT, where variance and covariance at each location of image space can be analytically derived, assuming a simple CT noise model. In modern CT scanners, helical scans with multi-detector rows are typically employed rather than the over-simplified 2D sequential fan-beam mode. The derivation of an analytical formula of noise (variance and covariance) in reconstructed images requires an accurate knowledge of reconstruction algorithms, which typically involve a rebinning process to convert cone-beam data to quasi-parallel-beam data and a weighted 3D filtered backprojection (FBP) process. Due to the complicated numerical operations in the reconstruction process, an accurate and fast derivation of noise in the final image may be difficult. Without losing generality, below we describe a relatively simpler and more efficient approach to obtain the noise distribution.

Figure 2:
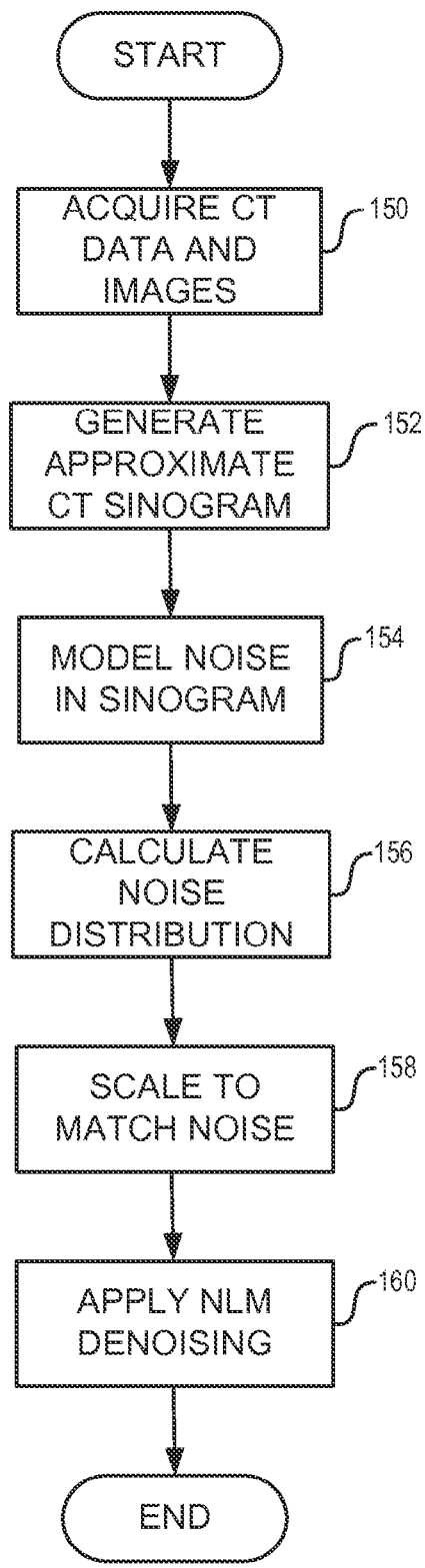
FIG. 2 is a flow chart setting forth the steps of processes for creating a noise map and utilizing the noise map in denoising.

The technique was based on estimating noise in each 2D slice separately with a fan beam approximation, which does not require access to the raw data, and therefore is computationally efficient and easily parallelizable for speed. Referring to FIG. 2, the basic process starts with "Acquiring CT data and reconstructing images" at process block 150. At process block 152, a CT sinogram, which may be an approximate sinogram, is generated. In principle, calculation of the sinogram relies upon accurate knowledge of the CT acquisition geometry. Here, the noise map estimation is preferably be fast, but can be approximate. A ray-driven forward projection method can be employed to generate the CT sinogram. The error in this approximation was demonstrated to be insignificant to affect the denoising results.

At process block 154, the noise in sinogram data is modeled. Although modern CT detectors are generally not photon-counting elements, but rather energy integrators that generate a signal proportional to the total energy deposited in the detector, a photon-counting model is still a good approximation of quantum noise and is widely used for characterizing noise properties of CT data. In simulations, after obtaining the CT sinogram, the transmitted photon map can be calculated by dividing the incident photon map by the exponential of the sinogram. The incident X-ray photon map can be a function of both detector bins and projection angle due to the influence of automatic exposure control (AEC) and bowtie filter. The effect of the bowtie filter can be characterized by measuring a map of noise-equivalent number of photons along the detector row from a set of air scans. The tube current modulation can be estimated based on the attenuation level along each projection angle and modulation strategy of the AEC system. One exemplary way to incorporate the effect of AEC and bowtie filter, and how to quantify the incident number of photons are available in Manduca, Yu et al. 2009, which is incorporated herein by reference.

At process block 156, the noise distribution in reconstructed images is calculated analytically. In one implementation, we calculated the analytical noise map based on a simple 2D fan-beam geometry and a rebinning filtered backprojection (FBP) reconstruction. (Examples of detailed derivation can be found in Pan and Yu 2003; Wunderlich and Noo 2008, which are incorporated herein by reference.)

At process block 158, the noise distribution is scaled to match the noise level in CT images. For proper denoising, the raw analytical noise map, which has arbitrary scaling due to the lack of knowledge of the actual number of input photons, is scaled to match the correct noise level in the CT image. This can be done in various ways. Below is an approach that is used in one implementation. The mean and standard deviation within 5×5 neighborhoods are calculated throughout the CT image. The standard deviations and the corresponding noise map values are compared for those points whose mean value falls within the range, for example, of −200 to +400 HU, and the relative scaling between the two that minimizes the summed-squared-difference between the two is determined by a golden-section-search optimizer. In homogeneous tissue, the measured standard deviations would be a noisy but accurate estimate of local noise levels. However, since real CT image can contain tissue heterogeneity or image structures, the calculated standard deviation (i.e. "noise") values are often too high, reflecting both actual noise and underlying heterogeneity. To minimize this bias, the summed-squared-difference calculations are trimmed to include only samples that fall within +/−10 HU of the corresponding scaled noise map values. In this way, erroneously high noise estimates can be rejected from the difference calculation during the optimization. The resulting scale value yields the best overall match between the (scaled) noise map and the estimated noise level in the CT image, without manual intervention.

At process block 160, a NLM denoising is performed that, for example, may be adaptive to the noise distribution. In this step, the noise distribution calculated in above steps is utilized during the NLM denoising process to generate noise-reduced images.

It is noted that the map of local noise level estimated from the above methods can also be used in many other filters to improve the noise reduction, and is not just limited to NLM filters. The method can be adopted to utilize a simple approximation to analytically calculate the noise map. Other methods can also be implemented to calculate the noise map, including incorporation of realistic CT geometry and reconstruction algorithms.

The present invention has been described in accordance with the embodiments shown, and one of ordinary skill in the art will readily recognize that there could be variations to the embodiments, and any variations would be within the spirit and scope of the present invention. For example, while above-described embodiments employed a map of local noise level as the basis for a denoising filter, the local noise spatial correlation can also be analytically derived and used for the purposes of denoising process. Accordingly, the adaptive filtering can be implemented based on local noise spatial correlation. Accordingly, many modifications may be made by one of ordinary skill in the art without departing from the spirit and scope of the appended claims.

The invention claimed is:

1. A method for reconstructing a computed tomography (CT) image of a subject, the method comprising:
    with a computed tomography (CT) imaging system, acquiring medical imaging data representing the subject that has been irradiated with a dose of radiation and reconstructing a CT image of the subject from said medical imaging data;
    calculating a raw analytical map of noise in a reconstructed CT image, said raw analytical map having arbitrary scaling;
    transforming the raw analytical map to a scaled map of noise that matches a spatial noise distribution at a local level of the reconstructed CT image; and
    forming a noise-reduced reconstructed CT image with the use of a denoising method applied to the reconstructed CT image and said spatial noise distribution at a local level of the reconstructed CT image.

2. The method of claim 1,
    wherein the calculating an analytical map of noise includes deriving a spatial noise distribution analytically by propagating noise through image reconstruction processes.

3. The method of claim 2,
    wherein the acquiring medical imaging data includes acquiring medical imaging data with the use of a CT acquisition geometry that includes at least one of a cone-beam geometry and a simple fan-beam geometry.

4. The method of claim 2,
    wherein the calculating an analytical map of noise includes accounting for influence of at least one of a bowtie filter and an automatic tube current modulation of the CT imaging system on photons transmitted through the subject.

5. The method of claim 1,
    wherein the forming includes forming a noise-reduced reconstructed CT image with the use of at least one of i) a non-local-means (NLM) filter; ii) a bilateral filter; and iii) an anisotropic diffusion filter, each of which has been adapted to a local noise level in the reconstructed CT image.

6. The method of claim 1,
    wherein said forming includes convolving values of pixels of the reconstructed CT image with an adaptive filter based on weight coefficients of the form $w(i,j)=\exp\{-\Sigma_{\delta \in P}G_\sigma(\delta)[v(i+\delta)-v(j+\delta)]^2/h^4\}$ that have been adapted to a local noise level in the reconstructed CT image,
    wherein G is a Gaussian kernel of variance $\sigma^2$, P denotes a patch of pixels centered at positions (i,j), and h is a smoothing coefficient,
    wherein the parameters a and h are adaptive to local noise distribution, and
    wherein values of pixels represent linear attenuation coefficients of material of the subject.

7. A computed tomography (CT) imaging system comprising:
    an x-ray source configured to emit x-rays toward an object to be imaged;
    a detector configured to receive x-rays that have been attenuated by the object;
    a data acquisition system (DAS) operably connected to the detector to receive a data input therefrom representing x-rays;
    a programmable computer system processor coupled to the DAS to receive an indication of received x-rays and programmed to:
        acquire medical imaging data representing the object positioned between the x-ray source and the detector and irradiated with radiation delivered from the x-ray source;
        form a reconstructed CT image from said medical imaging data; and
        create a reduced-noise CT image of the object by transforming, in an image domain, the reconstructed CT image with at least one of
            i) a non-local means (NLM) algorithm;
            ii) a bilateral filter algorithm; and
            iii) an anisotropic diffusion filter algorithm,
        each of which has been adapted to local variations of noise across the reconstructed CT image.

8. The CT imaging system of claim 7, wherein the processor is further programmed to:
    calculate a raw analytical map of noise in the reconstructed CT image, said raw analytical map having arbitrary scaling; and
    transform the raw analytical map to a scaled map of noise that matches a spatial noise distribution at a local level of the reconstructed CT image.

9. The CT imaging system of claim 8,
    wherein the calculating the raw analytical map of noise includes deriving a noise distribution analytically by propagating noise through image reconstruction processes.

10. A computed tomography (CT) imaging system comprising:
    an x-ray source configured to emit x-rays toward an object to be imaged;
    a detector configured to receive x-rays that have been attenuated by the object;
    a data acquisition system (DAS) operably connected to the detector to receive a data input therefrom representing x-rays;
    a computer system coupled to the DAS and programmed to:
        acquire medical imaging data representing a reconstructed CT image of the object positioned between the x-ray source and the detector and irradiated with radiation delivered from the x-ray source;
        determine a spatial distribution of the local level of noise in the reconstructed CT image; and
    generate a reduced-noise reconstructed CT image of the object by filtering said medical imaging data with a non-local means (NLM) filter that has been adapted to said distribution.

11. The system of claim 10, wherein the processor is programmed to convolve values of pixels of the reconstructed CT image with an adaptive filter based on weight coefficients of the form $$w(i,j) = \exp\left\{-\frac{\Sigma_{\delta \in P}G_\sigma(\delta)[v(i+\delta)-v(j+\delta)]^2}{h^4}\right\}$$

that have been adapted to a local noise level in the reconstructed CT image,
    wherein G is a Gaussian kernel of variance $\sigma^2$, P denotes a patch of pixels centered at positions (i,j), and h is a smoothing coefficient, and
    wherein values of pixels represent linear attenuation coefficients of material of the subject.

* * * * *